United States Patent [19]

Blaylock et al.

[11] Patent Number: 5,377,170

[45] Date of Patent: Dec. 27, 1994

[54] UTERAL CONTRACTION TIMER

[76] Inventors: Randy W. Blaylock, 5900 Lilley Rd., Ste. 10, Canton, Mich. 48187; John Kidd, 70053 Highway III, Rancho Mirage, Calif. 92270

[21] Appl. No.: 226,062

[22] Filed: Apr. 11, 1992

[51] Int. Cl.⁵ .............................................. G04E 8/00
[52] U.S. Cl. ................................. 368/110; 368/113
[58] Field of Search .................... 368/107–113, 368/250, 251; 128/660.01, 661.07–661.10

[56] References Cited

U.S. PATENT DOCUMENTS

| | | | |
|---|---|---|---|
| 3,946,312 | 3/1976 | Oswald et al. | |
| 4,000,466 | 12/1976 | Scouten et al. | |
| 4,077,011 | 2/1978 | Mathis | |
| 4,223,525 | 9/1980 | Jaunin | |
| 4,493,043 | 1/1985 | Forbath | 364/569 |
| 4,505,595 | 3/1985 | Rose et al. | |
| 4,623,265 | 11/1986 | Kamiyama | |
| 4,657,405 | 4/1987 | Nakazawa | |
| 4,711,585 | 12/1987 | Fresquez | 364/109 |
| 4,831,605 | 5/1989 | Suga | |
| 4,972,391 | 11/1990 | Juve et al. | |
| 5,088,497 | 2/1992 | Ikeda | 128/661.07 |
| 5,113,382 | 5/1992 | Bron | |
| 5,119,347 | 6/1992 | Portmann | |
| 5,119,349 | 6/1992 | Muto et al. | |
| 5,122,996 | 6/1992 | Sasaki et al. | |

Primary Examiner—Vit W. Miska
Attorney, Agent, or Firm—Gifford, Groh, Sprinkle, Patmore and Anderson

[57] ABSTRACT

A timer which measures the duration of a first of two consecutive contractions and also measures the elapsed time period between the beginning of said first contraction and the beginning of a second of two consecutive contractions and which displays successive pairs of first and second contractions and which also compares the most recent time measurement values to a user programmed target time and further alerts the user when a measured time is less than said programmed target time.

8 Claims, 2 Drawing Sheets

UTERAL CONTRACTION TIMER

BACKGROUND OF THE INVENTION

1. Field of the Invention

The present invention relates to a portable timer and in particular to a timer used to determined the duration of a first uteral contraction and the elapsed time between a first and a second uteral contraction experienced during childbirth.

2. Description of the Prior Art

As an expectant mother approaches delivering her child, she experiences numerous uteral contractions. The frequency of these contractions as well as their duration are of critical importance in determining how close the mother is to giving birth. Therefore, it becomes desirable to keep a log or history of both the duration of a single contraction as well as the distance between consecutive contractions. It is important that both of these values be recorded since the frequency of the contractions does not necessarily correlate to the length of the contractions. That is, simply because the contractions are more frequent does not necessarily mean that they last longer or vice versa.

The elapsed period between beginnings of subsequent contractions is commonly referred to as "how far apart" the contractions are, while the duration of a contraction is commonly referred to as the "length" of a contraction. Because physicians often instruct an expectant mother to proceed to a hospital after her contractions are a certain distance apart, one must, in addition to measuring the length of a single contraction, measure the distance between two contractions and compare it to the value prescribed by the physician. It is very cumbersome to monitor several pairs of consecutive contractions by using a conventional timing device since several time values must be recorded and operated on to determine the time between beginnings of two consecutive contractions. Moreover, without physically recording data relative to subsequent pairs of contractions, it is very difficult to monitor changes in contraction length and/or distances between consecutive pairs of contractions and then ultimately compare calculated distances apart to the target time value that was prescribed by the physician.

Conventional stop watches which measure only one event at a time are incapable of simultaneously calculating the distance between successive contractions. Even split time stop watches such as the one disclosed in U.S. Pat. No. 4,657,405 are not adapted to achieve the objects of the present invention. While the '405 patent describes an analog type stop watch which can measure the time of a first runner and the time of a second runner, for example, it is not adapted to display consecutive measured times of consecutive pairs of runners. The present invention, on the other hand, measures and displays a history of successive pairs of contractions. Finally, neither conventional nor split time stop watches are adapted to alert the user when the frequency of two events is greater than some preselected frequency.

3. Summary of the Present Invention

The present invention relates to a device which simultaneously measures and displays a plurality of pairs of measured times where the measured times include the elapsed period from the beginning of a first of two consecutive contractions to the beginning of the second contraction and the duration of said first contraction. Moreover, the present device comprises means for programming a user selected time interval representing some target time at which some further action must be taken. According to the present invention, said user selected target time is compared to the elapsed period between beginnings of consecutive contractions and warns the user if said elapsed time is less than said user selected target time.

BRIEF DESCRIPTION OF THE DRAWING

A better understanding of the present invention will be had upon reference to the following detailed description, when read in conjunction with the accompanying drawings, wherein like reference characters refer to like parts throughout the several views, and in which.

DETAILED DESCRIPTION OF THE PREFERRED EMBODIMENTS

Figure 1:
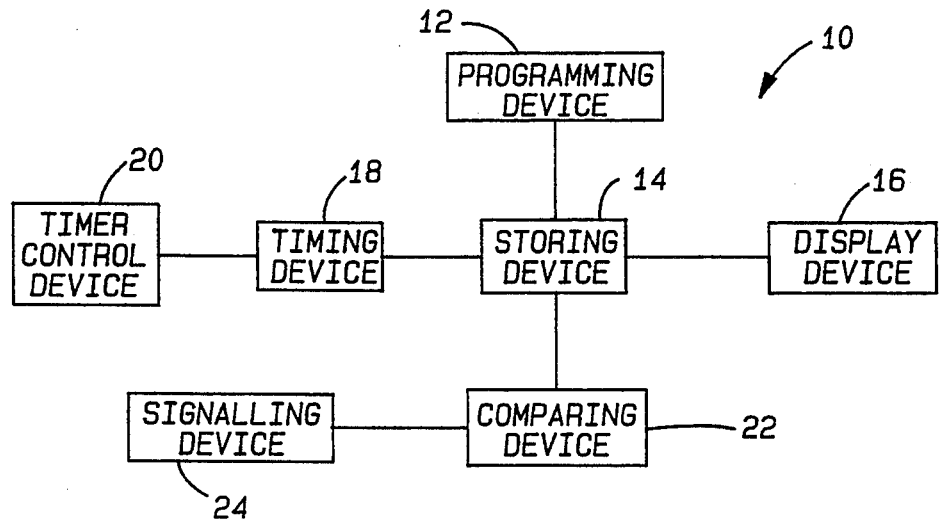
FIG. 1 is a block diagrammatic view of the present invention.
Figure 2:
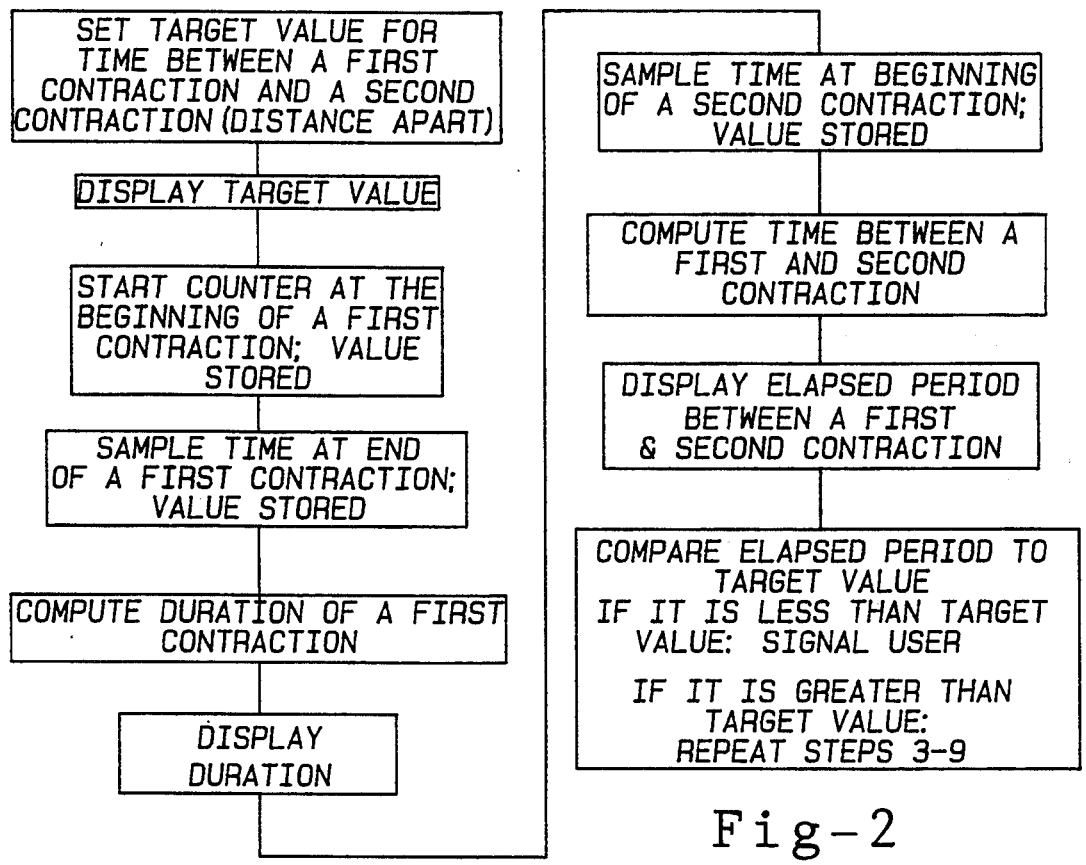
FIG. 2 is a flow chart illustrating the operation of a preferred embodiment according to the present invention.
Figure 3:
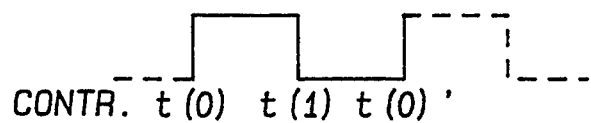
FIG. 3 is a timing diagram of a single time measurement interval.

Referring now to FIGS. 1–3, FIG. 1 depicts a block diagram of a contraction counter 10 according to the present invention and FIG. 2 presents a flowchart of its operation. FIG. 3 graphically depicts a single time measurement interval where $t(0)$ is the time at which a first of two consecutive contractions begins, $t(1)$ is the time at which said first contraction ends, and $t(0)'$ is the time at which a second of said two consecutive contractions begins.

As the flowchart of FIG. 2 indicates, before beginning a single time measurement interval, the user programs a target time representing a time at which some action must be taken. Thus, if the expectant mother is instructed by her physician to proceed to a hospital when her contractions are 4.5 apart, the user initiates programming means 12 by programming the target time as "4.5." This value is stored by storing means 14 and displayed by display means 16 of FIG. 1.

Referring again to FIG. 1, at the beginning of a first contractions the user initiates a timing device 18 by activating a timing control device 20 of the contraction counter 10 to measure a first time measurement interval. The measured time representing said beginning of a first contraction ($t(0)$ in FIG. 3) is stored by storing device 14. Timing device 18 continues timing until it receives a signal from control device 20 at time $t(1)$, the end of said first contraction. $T(1)$ is recorded by storing device 14 and the difference between $t(1)$ and $t(0)$ is calculated and displayed by display device 16 as the length of the first contraction. Control device 20 signals timing device 18 again at $t(0)'$, the beginning of the second contraction. $T(0)'$ is recorded by storing device 14 and the elapsed period between the beginning of the first contraction and the beginning of the second contraction is determined and displayed by display device 16 as the distance apart.

Of course, two independent timing devices could be employed to carry out the object of this invention without departing from the spirit of the invention. According to such an embodiment, after the predetermined target time is programmed both, independent timing devices would be activated at t(0) of FIG. 3. Thus, a first timing device would be started at t(0) and stopped at t(1); the second timing device, also beginning at t(0), would not be stopped until t(0)'. Consequently, the time measured by said first timing device would be the length of a first contraction while the time measured by said second timing device would be the distance between beginnings of two consecutive contractions.

The measured elapsed period between contractions is then compared to the stored target value by comparing device 22. If comparing device 22 determines that said elapsed period is less than the user selected target value, signaling device 24 is activated to signal the user. The user may choose to program another target time and begin another timing sequence. If, on the other hand, the measured elapsed period has not fallen below the target time value the user continues to measure and record data from successive pairs of contractions until said target time has been reached. Consequently, display device 16 will display successive lengths and elapsed times between pairs of consecutive contractions thereby providing the user with a history of measured times.

Figure 4:
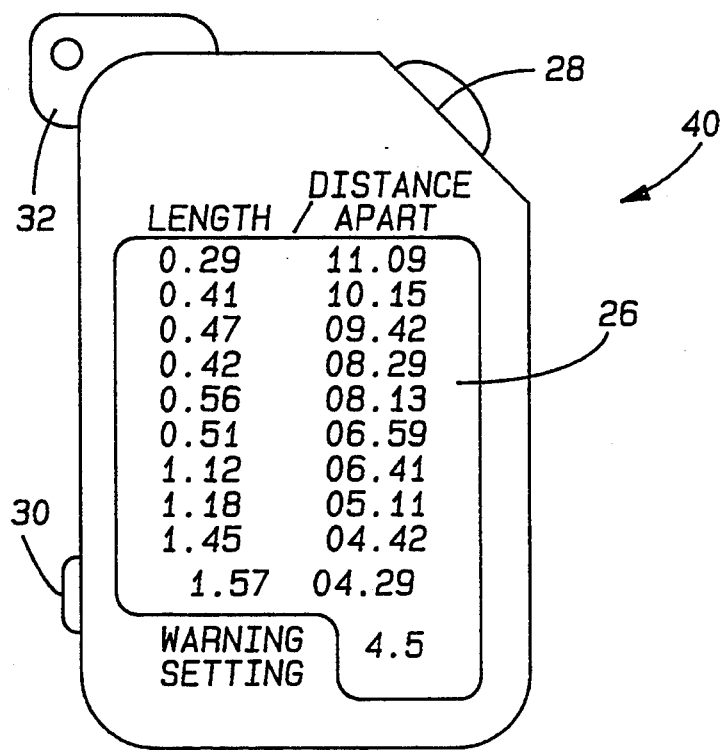
FIG. 4 is a top plan view illustrating a preferred embodiment of the present invention.

FIG. 4 depicts a preferred embodiment of the present invention where successive measurements are displayed on screen 26 in a columnar fashion. The measured duration of a first of two consecutive contractions is displayed in column "Length" while the measured elapsed period between said first and a second of said two consecutive contractions is displayed in column "Distance Apart." In a preferred embodiment, button 28 is used to initiate and control contraction counter 40 to measure the lengths and distances between pairs of contractions. Button 30 enables the user to program the target time value; in this example, the target time is 4.5 minutes. Although external buttons have been depicted in FIG. 4, any means suitable for programming and controlling the device may be substituted. The target time is displayed on screen 26 and is compared to the last displayed distance apart, in this case 4.29.

Once the value of the "distance apart" falls below the critical time value which was preprogrammed by the user, a warning signal such as an audible electronically generated sound (e.g. a beep or chirp) alerts the user that further action as prescribed by the physician should be taken. At anytime the user may choose to continue measuring successive contractions thereby repeating the above sequence.

To provide for convenient portable use, a preferred embodiment would further feature an eyelet 32 for a cord to be strung through the eyelet so that the contraction counter 40 could be hung around the user's neck.

Having described the invention, many modifications thereto will be come apparent to those skilled in the art to which it pertains without deviation from the spirit of the invention an defined by the scope of the appended claims.

We claim:

1. A portable contraction timer for operation by a user comprising:
   means for programming a user selected target time;
   means for timing to produce a plurality of pairs of measured times;
   means for controlling said timing means;
   means for displaying said plurality of pairs of measured times and said user selected target time;
   means for comparing said target time to said measured times;
   means for signaling the user when a measured time is less than said user selected target time.

2. A contraction timer as claimed in claim 1, wherein said pair of measured times includes the duration of a first of two consecutive contractions and the elapsed time from the beginning of said first contraction to the beginning of a second of two consecutive contractions.

3. A contraction timer as claimed in claim 2, wherein said means for displaying said plurality of pairs of measured times are successively displayed in a columnar fashion; wherein a first column successively displays successive measurements of said durations of a first of two consecutive contractions and a second column successively displays successive measurements of said elapsed period between a first and a second of two consecutive contractions.

4. A contraction timer as claimed in claim 1, wherein said means for controlling said timing means is an external button operated by the user at the beginning of a first contraction, at the end of a first contraction and at the beginning of a second contraction.

5. A means for controlling said timing means as claimed in claim 4, wherein said external button operated by the user is further operated to reset said timing means.

6. A contraction timer as claimed in claim 1, wherein said means for controlling said timing means comprises a plurality of switches operated by the user to activate said contraction timer, to reset said contraction timer, to measure said plurality of pairs of measured times.

7. A contraction timer as claimed in claim 1, wherein said means for displaying said plurality of pairs of measured times is an electronic digital display.

8. A contraction timer as claimed in claim 1, wherein said means for signaling the user is an electronically generated sound.

* * * * *